United States Patent [19]

Castaneda

[11] Patent Number: 4,596,780
[45] Date of Patent: Jun. 24, 1986

[54] PROCESS FOR SAMPLING AND DILUTING

[75] Inventor: Henry B. Castaneda, Woodbridge, Va.

[73] Assignee: Chemetrics, Inc., Warrenton, Va.

[21] Appl. No.: 686,213

[22] Filed: Dec. 26, 1984

Related U.S. Application Data

[62] Division of Ser. No. 475,975, Mar. 16, 1983, Pat. No. 4,537,747.

[51] Int. Cl.$^4$ .............................................. G01N 1/14
[52] U.S. Cl. .................................. 436/176; 436/179; 436/180
[58] Field of Search ........... 73/864.02, 864.12, 864.52; 141/4, 7, 9, 285; 422/100, 102; 436/180, 179, 176

[56] References Cited

U.S. PATENT DOCUMENTS

| | | | |
|---|---|---|---|
| 2,965,255 | 12/1960 | Gerarde | 73/864.02 X |
| 3,048,999 | 8/1962 | Pochan . | |
| 3,233,785 | 2/1966 | Burke | 73/864.02 |
| 3,285,296 | 11/1966 | Ishimaru et al. | 73/864.02 |
| 3,406,573 | 10/1968 | Burke | 73/864.02 |
| 3,464,800 | 9/1969 | Gerarde . | |
| 3,518,804 | 7/1970 | Gerarde . | |
| 3,603,156 | 9/1971 | Konkol . | |
| 3,618,393 | 11/1971 | Principe et al. . | |
| 3,634,038 | 1/1972 | Rampy . | |
| 3,676,076 | 7/1972 | Grady . | |
| 3,817,108 | 6/1974 | Principe et al. . | |
| 3,873,271 | 3/1975 | Young et al. . | |
| 4,124,044 | 11/1978 | Nugent . | |
| 4,332,769 | 6/1982 | Rampy et al. . | |

FOREIGN PATENT DOCUMENTS 46-19516  6/1971  Japan ................................. 73/864.02

OTHER PUBLICATIONS

Vacutainer Brand Tubes Product Information Sheet, "Laboratory Procedures Using the Unopette® Brand System," 8th Ed., ©1977, Becton Dickinson & Company, pp. 4 & 5.

Primary Examiner—Barry S. Richman
Assistant Examiner—Michael Gzybowski
Attorney, Agent, or Firm—Timothy R. Kroboth

[57] ABSTRACT

A process for sampling and diluting a liquid to be diluted utilizing a device comprising a hollow tubular body and a sealed pre-evacuated container. The hollow tubular body includes a self-filling tube for drawing up and capturing by capillary attraction a predetermined volume of a liquid to be diluted. Additionally, the hollow tubular body includes a connecting tube in an airtight sealing relationship with the self-filling tube. In a preferred embodiment, the container has a frangible tip for mutually interengaging in an air-tight sealing relationship with the connecting tube.

5 Claims, 3 Drawing Figures

U.S. Patent   Jun. 24, 1986   4,596,780
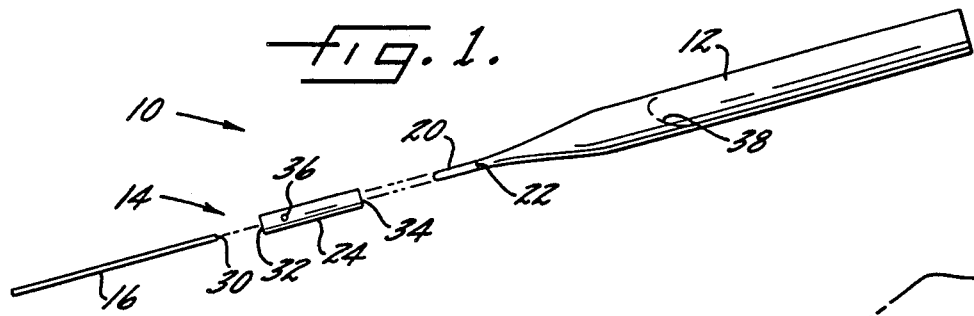
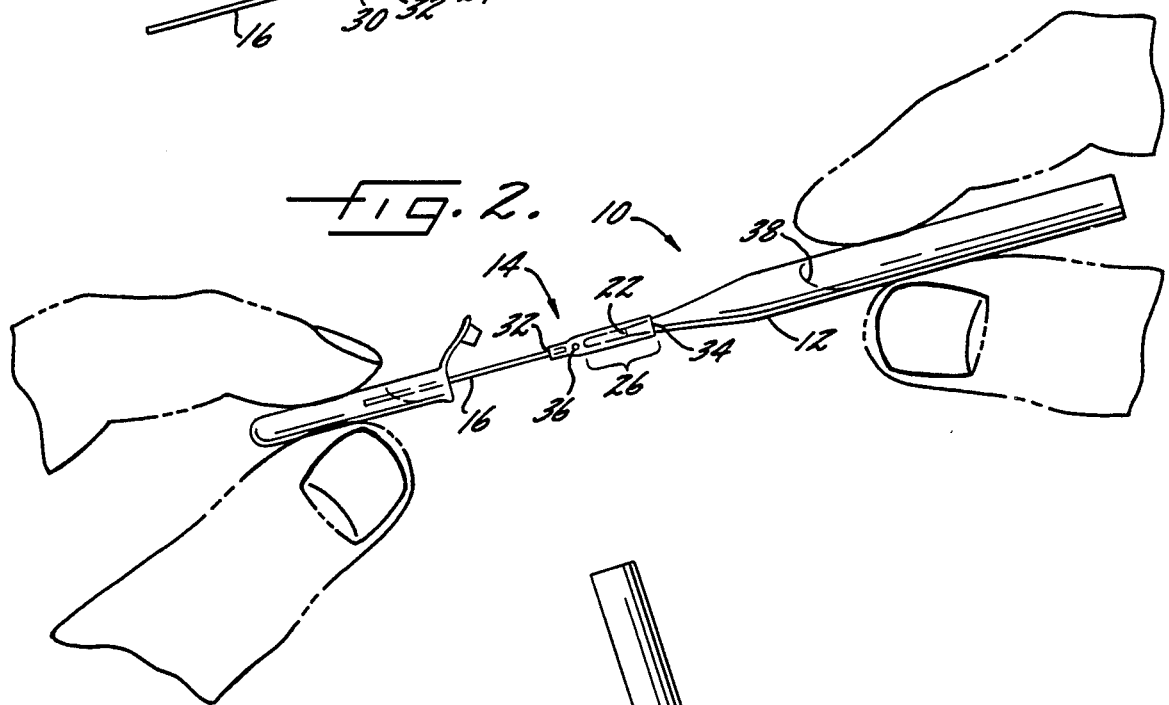
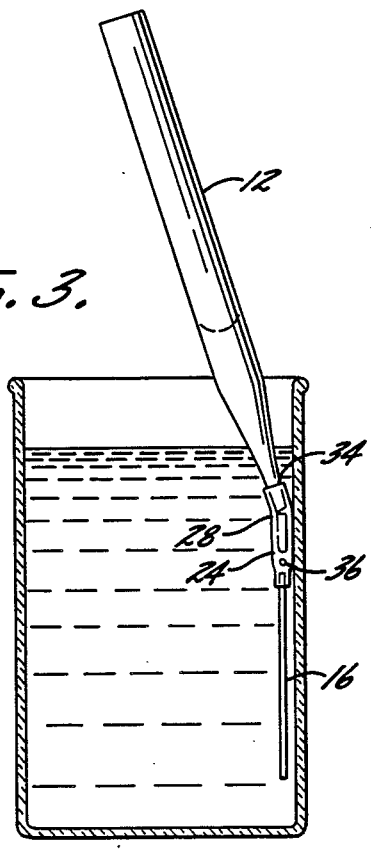

PROCESS FOR SAMPLING AND DILUTING

This is a division of application Ser. No. 475,975, filed Mar. 16, 1983, now U.S. Pat. No. 4,537,747.

TECHNICAL FIELD

This invention relates to the field of liquid dilution and more particularly relates to an accurate, disposable dilution device for use including clinical and industrial use. Furthermore, this invention relates to the quantitative chemical analysis of a liquid requiring dilution prior to the analysis thereof.

BACKGROUND ART

Mere sampling devices, as illustrated by U.S. Pat. Nos. 3,618,393 and 3,817,108 to Principe et al, are known. These particular sampling devices use an evacuated cannister having an inlet, a valve controlling the inlet, a gas tube connected to the inlet, and a one-way valve for obtaining a desired gaseous sample. Other mere sampling devices are illustrated by U.S. Pat. Nos. 3,464,800 and 3,518,804, both to Gerarde, as well as U.S. Pat. No. 3,873,271 to Young et al and Vacutainer Brand Tubes. The Gerarde patents show devices including, in each case, a capillary tube that is self-filled with a liquid, and a chamber connected to the capillary tube and having an opening 20. At column 4, lines 61–65, of the '804 patent, it is suggested that the liquid column may be transferred from the capillary tube to the chamber thereof by applying a mild aspirating force at end 20. The Young et al patent is directed to an apparatus for detecting free water in hydrocarbon fuels, and includes an evacuated container containing a reagent, and a cannula one end of which pierces through closure 22 so as to permit the fuel to be sampled, to be drawn into the container. The structure of the Vacutainer Brand Tubes, which can contain a diluent, is substantially the same as the apparatus of the Young et al patent.

Also known by me are pre-evacuated containers having a frangible tip, as illustrated by U.S. Pat. No. 3,634,038 to Rampy and U.S. Pat. No. 4,332,769 to Rampy et al. This latter patent is directed to a disposable titration device that includes a connector that tightly fits over the frangible tip of the container thereof, the connector having within it a rigid bead of a size suitable for effecting a leak-tight seal in the connector, and the connector being of a material readily deformable by finger pressure. Also known in the prior art is a device for measuring surface tensions and viscosities, as exemplified by U.S. Pat. No. 3,048,999 to Pochan. The device shown in FIG. 4 of this patent includes a capillary tube connected to a suction means in the form of a piston and cylinder, with a cock 25 in the communicating line. In using this device, a sample is drawn up the capillary tube by use of the suction means thereof. At column 4 of this patent, cleaning of the capillary tube is described as involving passing a series of cleaning fluids through the capillary tube to a plug 24 of absorbent material.

In the prior art, sampling and diluting devices are known, as illustrated by U.S. Pat. Nos. 3,603,156 to Konkol, 3,676,076 to Grady, and 4,124,044 to Nugent, and the Unopette ® device of Becton Dickinson. Each of these devices includes a capillary tube that is filled with a sample and a tube connected thereto having an opening. Dilution is effected in the Konkol and Grady devices by physically shaking the sample out of the capillary tube into a diluent; whereas, in the Nugent and Unopette ® devices, a resilient container containing a diluent is squeezed slightly and the capillary tube is inserted into the container so that when pressure is released on the container, negative pressure draws the sample into the diluent. Also known in the prior art are dilution pipettes, which are used by drawing up the liquid to be diluted into the pipette by suction, closing the end to which the suction was applied, lowering the pipette into a diluent, and again applying suction until the total volume of fluid in the pipette reaches a certain calibration. The pipette is then shaken to effect dilution. Unfortunately, use of a dilution pipette is a slow and tedious way to obtain a specific dilution, the accuracy of the dilution depending upon the skill of the technician.

This art and all prior art of which I am aware, fails to provide a disposable device for sampling and diluting of a liquid to be diluted, and a process for sampling and diluting of the liquid, that are capable of providing an accurate dilution of a small volume of a liquid to be diluted, a wide-ranging dilution ratio on the order of from about 1:25 up to about 1:10,000 by appropriate equipment selection, and quantitative flushing of the liquid into a container by use of a diluent simultaneously with effecting a predetermined dilution of the liquid in the container. Additionally, this art does not provide a device and process of this type that make possible a rapid dilution. Furthermore, this art does not provide a device of this type that is capable of functioning as a "seal" between the diluted liquid and the ambient atmosphere. Moreover, this art does not provide a device of this type that, when easily modified after having been used for diluting the liquid, is suitable for storage and transportation of the diluted liquid and also can be used to dispense the diluted liquid in a drop-by-drop manner. Also, this art does not provide a device and process of this type, that are useful for sampling, diluting and analyzing.

SUMMARY OF THE INVENTION

It is accordingly an object of the present invention to provide a disposable device for sampling and diluting of a liquid to be diluted and a process for sampling and diluting of the liquid, that are capable of providing an accurate dilution of a small volume of a liquid to be diluted, a wide-ranging dilution ratio on the order of from about 1:25 up to about 1:10,000, and quantitative flushing of the liquid into a container by use of a diluent simultaneously with effecting a predetermined dilution of the liquid in the container.

It is a further object to provide a device and process of this type that make possible a rapid dilution.

It is a still further object to provide a device of this type capable of functioning as a "seal" between the diluted liquid and the ambient atmosphere.

It is an even further object to provide a device of this type that when easily modified after having been used to effect a dilution, is suitable for storage and transportation of the diluted liquid and also can be used to dispense the diluted liquid in a drop-by-drop manner.

It is an additional object of the present invention to provide a device and process of this type useful for sampling, diluting and analyzing.

Other objects and advantages of the present invention will become apparent as the description thereof proceeds.

In satisfaction of the foregoing objects and objectives, a disposable device for sampling and diluting of a liquid to be diluted, includes a hollow tubular body that includes a self-filling tube for drawing up and capturing by capillary attraction a predetermined volume of a liquid to be diluted; and that further includes a connecting tube in an air-tight sealing relationship with an upper end of the self-filling tube. The device further includes a sealed pre-evacuated container having a fill volume selected to effect a predetermined dilution of the liquid captured by the self-filling tube. The container has means for mutually interengaging in an air-tight sealing relationship with the connecting tube. The device furthermore includes means for providing ready communication between the interior of the container and the hollow tubular body when the container and the connecting tube are in an air-tight sealing relationship. Also included in the device is means for preventing air pressure build-up within the hollow tubular body that would preclude the drawing up of the predetermined volume of a liquid to be diluted, or that would overcome the liquid capturing capability of the self-filling tube.

Also provided is a process for sampling and diluting of a liquid to be diluted. The process includes the steps of drawing up and capturing by capillary attraction a predetermined volume of a liquid to be diluted, and applying a vacuum to cause a diluent to quantitatively flush the captured liquid into a container and also to effect a predetermined dilution of the captured liquid in the container.

In the description of the drawing and in the detailed discussion of the invention which follows, there is shown and essentially described only the preferred embodiment of the invention, simply by way of illustration of the best mode contemplated of carrying out the invention. As will be realized, the invention is capable of other and different embodiments, and its several details are capable of modification in various respects, all without departing from the invention. Accordingly, the drawing and description are to be regarded as illustrative in nature, and not as restrictive.

BRIEF DESCRIPTION OF DRAWING

Reference is hereby made to the accompanying drawing, which forms a part of the specification of the present invention.

FIG. 1 is an exploded view of the device of the present invention, with the hollow tubular body shown separate from the pre-evacuated container;

FIG. 2 is a perspective view showing the device shown in FIG. 1 assembled for use and being used to draw up a liquid to be diluted from a micro-test tube; and FIG. 3 is a perspective view showing the manner in which the device is typically inserted into a diluent.

BEST MODE FOR CARRYING OUT THE INVENTION

Referring to the Figures, a preferred sampling and diluting device 10 in accordance with the present invention, comprises a sealed evacuated container 12 and a hollow tubular body 14. The hollow tubular body includes a self-filling tube 16 that has an internal diameter selected to draw up by self-filling, a predetermined volume of a liquid to be diluted, and to capture the drawn up liquid. The entire length or less than the entire length of tube 16 may be self-filled to provide the predetermined volume. When the entire length is self-filled, filling of the tube will stop automatically when the liquid reaches the end of the tube opposite the tip thereof. If less than the entire length is filled, tube 16 is advantageously filled to an indicator mark. Tube 16 is preferably of glass, but may be of any material capable of drawing up and capturing by capillary attraction a liquid to be diluted. By "capturing" is meant that the capillary attraction acts to prevent the drawn up liquid from exiting from the tube tip in response to mere gravitational force. When the liquid to be drawn up for subsequent dilution is aqueous, tube 16 will be of glass, and thus one may use a commercially available glass capillary tube of appropriate internal diameter by, for example, cutting the tube to a suitable length. Preferably, tube 16 is transparent or translucent, but it may be opaque.

Container 12 is partially or completely evacuated of air. The degree of evacuation and the size of the container are selected to provide container 12 with a fill volume that will effect a predetermined dilution of the liquid captured by the self-filling tube. The following table shows the relationship between internal diameter, length and volume of the self-filling tube, and further shows the dilution ratio that will result when tube 16 completely filled with the liquid to be diluted, is used with an evacuated container having a fill volume of 1.3 ml.

| Internal Diameter (mm) | Length (mm) | Volume (Microliters) | Dilution Ratio |
|---|---|---|---|
| 0.67 | 37.2 | 13.0 | 1:100 |
| 0.67 | 18.6 | 6.5 | 1:200 |
| 0.50 | 11.0 | 2.2 | 1:600 |

As indicated by the table, the volume of liquid drawn up by tube 16 will be typically small, i.e., on the order of from about 1 or 2 up to about 50 microliters. A convenient size container will be about 7.0 to about 25 mm in outside diameter. Accordingly, device 10 will be able to provide a wide-ranging dilution ratio on the order of from about 1:25 up to about 1:10,000.

A container having a fill volume of 1.3 ml advantageously has a length of about 97 mm and an outside diameter of about 7.1 mm.

As is explained in more detail below, the device of this invention is also useful as a sample diluting and analyzing device, in which case a fill volume of about 8 ml will enable instrumental analysis.

In general, I prefer to evacuate container 12 to a pressure of about 40 millimeters absolute. The container is preferably of glass, but may be of any material that can be drawn out to a readily frangible tip and sealed at the tip. The peripheral wall of the container should be of sufficient strength to permit ready handling. A wall of ordinary test tube glass on the order of about 0.5 to 1 mm is adequate for this purpose. One end of the container is drawn out in a slender, thin-walled, frangible tip 20 that preferably has a score mark 22, which insures breaking of tip 20 at that point when finger pressure is applied thereto. Conveniently, the taper is drawn to about 2 mm in outside diameter, and the score mark will be about 3 to 10 mm from the actual tip.

Hollow tubular body 14 also includes a connecting tube 24 that is advantageously a common heat shrinkable, finger pressure-deformable polyethylene tubing.

Tubing of this type is available commercially from a number of sources including Sinclair and Rush. However, the connecting tube may be of any material sufficiently deformable to permit, when container 12 and the connecting tube are in an air-tight sealing relationship, a portion 26 of frangible tip 20 located within the connecting tube to be broken readily by finger pressure exerted through a tubular wall 28 of the connecting tube. By applying heat to the polyethylene tubing while having an upper end 30 of the self-filling tube within an end 32 of the polyethylene tubing, an air-tight seal is formed between the connecting tube and the self-filling tube. The other end 34 of the connecting tube is of an internal diameter relative to the outside diameter of slender tip 20 that enables end 34 to fit over portion 26 of the slender tip and form an air-tight seal between end 34 and the tip in a region above score mark 22. The connecting tube is conveniently about ¾ inch in length, for a container having a filled volume of about 1.3 ml.

In order to prevent air pressure build-up within hollow tubular body 14, a two-way vent port 36 is preferably provided. Alternatively, the dead space volume provided by the tubular body could be made large enough to prevent any such air pressure build-up. Port 36 serves to readily vent otherwise trapped air from within the hollow tubular body to the ambient atmosphere. Being two-way, the vent port will also act as a bypass to permit liquid flow into tubular body 14. This flow is advantageous in that, as will be better understood from the description below, rapid fill of container 12 with a diluent is made possible. Port 36 is preferably located in tubular wall 28, the location being below the region of the air-tight sealing relationship between the connecting tube and the container, and above the region of the air-tight sealing relationship between the connecting tube and the self-filling tube. The vent port could alternatively be located in the wall of the self-filling tube above a level to which it is desired to self-fill tube 16. Port 36 is conveniently circular but could be of any shape.

The vent port may be of any diameter that readily permits escape to the ambient atmosphere of air which would otherwise be compressed inside tubular body 14. Preferably, the vent port should, however, not be so large that the diluent almost entirely bypasses tube 16 to enter container 12 through port 36. A very small diameter of port 36, say less than about 0.5 mm, would unnecessarily retard filling of the container by the diluent. Thus, a reasonable, practical range for the diameter will be from about 0.5 to 1.5 mm when the fill volume of container 12 is about 1 ml, and from about 1 to 2 mm when the fill volume is about 5 ml. These diameters will enable the container to be filled in a few seconds, and will additionally be appropriate to insure quantitative flushing of the captured liquid into the container.

Instead of a two-way vent port, a self-closing, one-way valve could be provided in tubular wall 28 that would close upon applying vacuum from container 12 to tubular body 14. An illustrative valve generally of this type is shown in U.S. Pat. No. 3,817,108; however, it is to be understood that for this valve to be practicable in device 10, connecting tube 24 would need to be of a material in the area of the valve sufficiently sensitive to open in response to a rather small degree of air pressure build-up within tubular body 14.

The Figures show only one vent port 36. However, more two-way vent ports or one-way valves could be used, but one is typically adequate.

In use, end 34 of connecting tube 24 is fit over portion 26 of slender tip 20 to form the air-tight seal above score mark 22, and a predetermined volume of a liquid to be diluted is drawn up and captured by capillary attraction by introducing a tip portion of the self-filling tube into the liquid. Vent port 36 allows air to escape from within tubular body 14 as tube 16 fills with the liquid, and thereby prevents air pressure build-up that would preclude the drawing up of the predetermined volume. When the predetermined volume is provided by the entire length of tube 16 being self-filled, tube 16 is conveniently oriented almost horizontally for a very short time, with the requisite time for self-filling depending upon factors such as the internal diameter and length of the self-filling tube. Other orientations of the tube could be appropriate if it is desired to allow tube 16 to self-fill incompletely. When completely filling tube 16, the connecting tube is preferably transparent or translucent so as to allow for visual observation of complete filling of upper end 30 of tube 16. Another way of providing for visual observation of complete filling is to use port 36 also as an inspection port, when port 36 is of sufficiently large diameter to serve this additional function.

After self-filled tube 16 has been withdrawn from contact with the liquid to be diluted, and tube 16 and at least the portion of connecting tube 24 having port 36 have been inserted into a diluent, a vacuum is applied to tubular body 14 from pre-evacuated container 12 to cause the diluent to quantitatively flush the predetermined volume of liquid drawn up and captured by the self-filling tube into the container, and furthermore to effect a predetermined dilution of the captured liquid. By "vacuum" is meant that most or all of the air or gas has been removed from container 12. The vacuum is applied by breaking frangible tip 20 by finger pressure exerted through tubular wall 28 of the connecting tube. Port 36 is maintained below the upper surface of the diluent to insure that no air is drawn into container 12 in lieu of diluent. As an alternative to maintaining port 36 submerged in the diluent, port 36 could be closed off as by pressing a finger over the port after the frangible tip has been broken, until all diluent has been drawn into container 12.

Alternatively, use of the device of the invention could be modified as in the below-described manner. One could form the air-tight seal between the evacuated container and the connecting tube after inserting the self-filled tube in the diluent, rather than forming the seal at the outset. When the device of the present invention is used in this manner, the two-way vent port prevents pressure build-up within the hollow tubular body that would overcome the liquid capturing capability of the self-filling tube and thereby expel any of the drawn up liquid from the self-filling tube.

After using device 10 for sampling and diluting, the device may simply be set aside for later analysis of the diluted liquid, with tube 16 then functioning as a "seal" between the diluted liquid and the ambient atmosphere. When the technician is ready to analyze the diluted liquid, the contents of container 12 are readily accessed by, for example, pulling end 34 of the connecting tube out of its sealing fit with tip 20 of the container. Alternatively, when it is desired to store the diluted liquid in container 12 for a substantial period of time, container 12 could be more permanently sealed by fitting a plastic cap over tip 20 after disconnection of end 34. This more permanently sealed container is highly suitable for being transported, particularly since container 12 may be readily handled. One mode of accessing the contents of container 12 is by syringe. Another useful mode, where for example the liquid to be diluted is blood and it is desired to analyze for white blood cells, is by cutting connecting tube 24 at a point between the original actual tip of tip 20 and upper end 30 of the self-filling tube, and then physically shaking a drop of sample out of container 12, for example, onto a slide. Thus, it can be seen that this device is suitable for storage and transportation of the diluted liquid, and furthermore can be used to dispense the diluted liquid in a drop-by-drop manner.

In another application of the device of this invention for sampling and diluting, a predetermined quantity of an additive 38 such as a stabilizing agent for the diluted liquid is provided within container 12. As a result, stabilization of the diluted liquid also occurs when liquid dilution is effected.

In addition to being useful as a liquid sampling and diluting device, the device of this invention is useful as a sample diluting and analyzing device. In this use, container 12 is provided with a predetermined quantity of additive 38, which is a reagent for a desired analysis. Thus, a sample is diluted to extend the test range, and mixed with an appropriate analytical reagent at the same time. This use quickly achieves dilution and analysis with a minimum of equipment. When the reagent is a colorimetric reagent, container 12 is of a suitable transparent material. Otherwise, container 12 may be of an appropriate translucent or opaque material.

In this description, there is shown and essentially described only the preferred embodiment of the invention, but as mentioned above, it is to be understood that the invention is capable of changes or modifications within the scope of the inventive concept expressed herein. Several changes or modifications have been briefly mentioned for purposes of illustration. In addition, it can be seen that a sealed pre-evacuated container of the type described in the Young et al patent could be used in combination with a hollow tubular body having a pointed end for piercing the flexible closure of that type of pre-evacuated container. Unlike the preferred embodiment described, a portion of the hollow tubular body thereof would not need to be deformable.

INDUSTRIAL APPLICABILITY

The device and process of this invention are useful for industrial applications including dilution of a brine water sample such as is obtained in oil well drilling. In one aspect of the invention, the brine water sample is diluted and simultaneously mixed with an analytical reagent.

I claim:

1. A process for sampling and diluting a liquid to be diluted, said process comprising:
   drawing into, and capturing in, a hollow tubular member by capillary attraction, a predetermined volume of a liquid to be diluted, said hollow tubular member having a two-way vent port therein,
   inserting the captured liquid-containing tubular member into a liquid diluent so as to submerge said two-way vent port, and
   while maintaining said two-way vent port submerged, applying a vacuum to said captured liquid-containing tubular member, from a sealed pre-evacuated container having a fill volume selected to effect a predetermined dilution of said captured liquid, whereby said captured liquid is completely flushed into said container by diluent drawn through the tubular member, rapid fill of said container with diluent is provided, and said predetermined dilution is effected.

2. The process of claim 1, wherein said container contains a predetermined quantity of a reagent for a desired analysis, whereby the vacuum-applying step further results in mixing of the diluted liquid with said reagent.

3. The process of claim 1, wherein said container contains a predetermined quantity of a stabilizing agent for the diluted liquid, whereby the vacuum-applying step further results in mixing of the diluted liquid with said stabilizing agent.

4. A fast, simple process for sampling and diluting prior to analysis, a liquid sample requiring dilution prior to said analysis, said process comprising
   drawing into, and capturing in, a hollow tubular member by capillary attraction, a predetermined volume of a liquid to be diluted, said hollow tubular member having a two-way vent port therein;
   inserting the captured liquid-containing tubular member into a liquid diluent so as to submerge said two-way vent port;
   while maintaining said two-way vent port submerged, applying a vacuum to said captured liquid-containing tubular member, from a sealed pre-evacuated container that is in an air-tight sealing relationship with the tubular member and that has a full volume selected to effect a predetermined dilution of said captured liquid, whereby said captured liquid is completely flushed into said container by diluent drawn through the tubular member, rapid fill of said container with diluent is provided, and said predetermined dilution is effected; and
   disengaging said hollow tubular member from said air-tight sealing relationship with said container, whereby the diluted liquid within said container is rendered readily accessible for analysis.

5. A fast, simple process for sampling, diluting and dispensing for analysis, a liquid sample requiring diluting prior to said analysis, said process comprising
   drawing into, and capturing in, a tube member of a hollow tubular body by capillary attraction, a predetermined volume of a liquid to be diluted;
   inserting into a liquid diluent the captured liquid-containing tubular body, which further comprises a connecting tube, so as to submerge a two-way vent port located in said connecting tube;
   while maintaining said two-way vent port submerged, applying a vacuum to said captured liquid-containing tubular body, from a sealed pre-evacuated container that is in an air-tight sealing relationship with the tubular body through said connecting tube and that has a fill volume selected to effect a predetermined dilution of said captured liquid, whereby said captured liquid is completely flushed into said container by diluent drawn through the tubular body, rapid fill of said container with diluent is provided, and said predetermined dilution is effected;
   cutting said connecting tube to separate said tube member from said container; and
   dispensing a drop of the diluted liquid from said container by physically shaking said container.

* * * * *